United States Patent
Kawakami et al.

(10) Patent No.: US 8,440,179 B2
(45) Date of Patent: *May 14, 2013

(54) AGENT FOR REDUCING VISCERAL FAT

(75) Inventors: Hiroshi Kawakami, Kawagoe (JP); Yasuhiko Shiinoki, Kawagoe (JP); Yukio Kadooka, Kawagoe (JP)

(73) Assignee: Megmilk Snow Brand Co., Ltd., Sapporo (JP)

( * ) Notice: Subject to any disclaimer, the term of this patent is extended or adjusted under 35 U.S.C. 154(b) by 617 days.

This patent is subject to a terminal disclaimer.

(21) Appl. No.: 12/525,172

(22) PCT Filed: Feb. 29, 2008

(86) PCT No.: PCT/JP2008/053665
§ 371 (c)(1), (2), (4) Date: Sep. 28, 2009

(87) PCT Pub. No.: WO2008/108298
PCT Pub. Date: Sep. 12, 2008

(65) Prior Publication Data
US 2010/0021445 A1    Jan. 28, 2010

(30) Foreign Application Priority Data
Mar. 2, 2007 (JP) ................ 2007-053179

(51) Int. Cl.
A61K 35/74 (2006.01)
A23K 1/16 (2006.01)
A23C 19/032 (2006.01)
A61P 3/04 (2006.01)

(52) U.S. Cl.
USPC .......... 424/93.45; 435/252.9; 514/909; 426/61; 426/71

(58) Field of Classification Search ........ 424/93.45; 435/252.9; 426/61, 71; 514/909
See application file for complete search history.

(56) References Cited

U.S. PATENT DOCUMENTS
3,827,940 A * 8/1974 Sugimoto et al. .......... 435/210

FOREIGN PATENT DOCUMENTS

| JP | 08-268899 | 10/1996 |
| JP | 10-045610 | 2/1998 |
| JP | 11-098978 | 4/1999 |
| JP | 2003-095963 | 4/2003 |
| JP | 2003-252770 | 9/2003 |
| JP | 2003-306436 | 10/2003 |
| JP | 2004-099539 | 4/2004 |
| JP | 2004-315477 | 11/2004 |
| JP | 2006-069993 | 3/2006 |
| JP | 2006-076961 | 3/2006 |
| JP | 2006-182654 | 7/2006 |
| JP | 2006-304792 | 11/2006 |
| WO | WO 02/38165 A1 | 5/2002 |
| WO | WO 2006/084381 A1 | 8/2006 |

OTHER PUBLICATIONS

Abdominal Obesity from Metabolic Syndrome Facts. downloaded on Feb. 28, 2012 from http://metabolicsyndromefacts.com/article/abdominal-obesity-central-obesity. p. 1-2.*
Fungi. UNM Biology Undergraduate Labs. downloaded on Feb. 29, 2012 from http://biology.unm.edu/ccouncil/Biology_203/Summaries/Fungi.htm. p. 1-9.*
Metabolic Syndrome. PubMed Health. Jun. 28, 2011 downloaded from http://www.ncbi.nlm.nih.gov/pubmedhealth/PMH0004546/ p. 1-4.*
Takashi et al. English translation of JP2004-099539 p. 1-4 (machine translation).*
Zemel et al. Dairy augmentation of total and central fat loss in obese subjects. International Journal of Obesity (2005) 29, 391-397.*
Yoplait. Dairy & Digestion, The Benefits of Yogurt. downloaded on Mar. 1, 2012 from http://yoplait.com/living-healthy/benefits-of-yogurt/diary-and-digestion?print=true. p. 1.*
Vasiljevic, T. and Shah, N. P. (2006) Fermented Milk: Health Benefits Beyond Probiotic Effect, in Handbook of Food Products Manufacturing (ed Y. H. Hui), John Wiley & Sons, Inc., Hoboken, NJ, USA. p. 99-115.*
Despres and Lemieux. Abdominal obesity and metabolic syndrome. Nature. vol. 444, p. 881-887. 2006.*
Hiroshi Kawakami, "New Health Claims of Cheese," Livestock Information, [domestic edition] Feb. 2007, pp. 22-29.
Y. Nakamura et al.,"Antihypertensive Effect of Sour Milk and Peptides Isolated from it That are inhibitors to Angiotensin I-Converting Enzyme," Journal of Dairy Science vol. 78, No. 6, 1995, pp. 1253-1257.
Y. Nakamura et al.,"Purification and Characterization of Angiotensin I-Vonverting Enzyme Inhibitors from Sour Milk," Journal of Dairy Science vol. 78, No. 4, 1995, pp. 777-783.
Supplementary European Search Report issued by European Patent Office on Oct. 6, 2010 for the counterpart European Patent Application No. 08721085.2.

* cited by examiner

Primary Examiner — Taeyoon Kim
(74) Attorney, Agent, or Firm — Knobbe, Martens, Olson & Bear LLP

(57) ABSTRACT

Provide a visceral fat reducing agent for reducing the diseases and conditions associated with the metabolic syndrome which represents a condition where various risk factors such as those for hypertension, hyperlipemia, glucose tolerance dysfunction, etc., have accumulated, or simply reducing an accumulation of visceral fat, wherein the effective ingredient of said visceral fat reducing agent includes fungus bodies of lactic bacteria, especially lactic bacteria belonging to the *Lactobacillus* sp. and *Lactococcus* sp. and/or cultures thereof, while also providing a beverage, food or feed containing said visceral fat reducing agent.

7 Claims, No Drawings

AGENT FOR REDUCING VISCERAL FAT

This application is the U.S. National Phase under 35 U.S.C. §371 of International Application PCT/JP2008/053665, filed Feb. 29, 2008, which claims priority to Japanese Patent Application No. 2007-053179, filed Mar. 2, 2007. The International Application was published under PCT Article 21(2) in a language other than English

TECHNICAL FIELD

The present invention relates to a visceral fat reducing agent whose effective ingredient includes fungus bodies of lactic bacteria, especially lactic bacteria belonging to the *Lactobacillus* sp. and *Lactococcus* sp., and/or cultures thereof. The present invention also relates to a new beverage, food or feed that has been blended with the aforementioned visceral fat reducing agent to add a visceral fat reducing action.

An accumulation of visceral fat is considered as a cause of the metabolic syndrome, which in turn is believed to trigger eventual thrombosis, insulin resistance, anomaly of saccharometabolism, hypertension and other circulatory diseases. When taken, a visceral fat reducing agent conforming to the present invention is effective in reducing the accumulated visceral fat and thereby preventing/treating the metabolic syndrome.

BACKGROUND ART

In recent years, the population of people exhibiting symptoms of diabetes, hypertension, hyperlipemia, arteriosclerosis and other diseases and conditions that are referred to as "diseases associated with adult lifestyle habits" has been increasing in Japan as a result of westernization of traditional lifestyle habits. In particular, cardiovascular diseases and cerebrovascular diseases account for approx. one-third of all deaths, and this ratio is increasing each year. Accordingly, implementing measures to address these diseases has become a national challenge. With these arteriosclerotic diseases, the risk of pathogenesis increases significantly when hypertension, hyperlipemia, glucose tolerance dysfunction and other risk factors accumulate. The condition where these risk factors have accumulated is called the "Metabolic Syndrome," which is a widely recognized medical condition.

According to a study of 120,000 Japanese working at corporations, those who have at least one of the risk factors "Obesity," "Hypertension," "High blood sugar," "High triglyceride (neutral fat) blood disease" and "Hypercholesterolemia" are said to have a five times higher risk of developing heart diseases. The risk of heart diseases increases ten-folds with those having two risk factors, and it rises as much as 31 times with those having three to four risk factors. According to a study conducted by the Ministry of Health, Labour and Welfare of Japan, there are reportedly 39 million people suffering from hypertension, 22 million people suffering from hyperlipemia, 1.62 million people suffering from diabetes (including those not currently suffering from diabetes but presenting higher risks of developing one), and 4.68 million people suffering from obesity. The numbers of these patients are increasing each year.

The metabolic syndrome is a "Multiple risk factor syndrome that tends to cause arteriosclerosis, characterized by accumulation of visceral fat as well as by association with multiple diseases including insulin resistance, anomaly of saccharometabolism, lipid metabolism abnormality and hypertension resulting from accumulation of visceral fat." An accumulation of visceral fat is the very fundamental cause of the metabolic syndrome. Fat tissues, which are secretory tissues covering the largest area in the living body, produce various endocrine factors and play a part in the maintenance of homeostasis in the living body. However, studies have revealed that an excessive accumulation of visceral fat can tip the secretion balance of endocrine factors and cause various diseases and conditions. In particular, certain endocrine factors such as plasminogen activator inhibitor (PAI-1), tumor necrotizing factor (TNF-α), reptin, etc., are secreted in greater amounts as visceral fat accumulates, and higher secretion levels of these endocrine factors cause thrombosis, insulin resistance, anomaly of saccharometabolism, hypertension, and so on.

In the meantime, adiponectine, which is uniquely secreted by fat tissues, is normally present at a high concentration in blood streams. It is known that when visceral fat accumulates, the concentration level of adiponectine decreases. Adiponectine is known to have various physiological functions such as anti-diabetic action, anti-arteriosclerotic action, anti-inflammatory action, and anti-hypertensive action, and therefore it is very important to promote an increase in the adiponectine level in blood streams, or suppress a decrease in the adiponectine level in blood streams, in order to prevent/treat the metabolic syndrome.

Drug therapies have traditionally been used to counter the individual diseases and conditions caused by the metabolic syndrome, but these therapies present problems in that, among others, they require prescriptions and also accompany side effects. In addition, it has been shown that even when one disease or condition is treated, other disease or condition may develop into a serious state. Accordingly, it is necessary to adjust the secretion balance of endocrine factors which are derived from fat cells present upstream of these conditions.

In view of the above, it is considered more important to change our daily lifestyle habits such as exercise and diet, rather than resorting to drag therapies, in the prevention/treatment of the metabolic syndrome caused by an accumulation of metabolic fact. For this reason, drugs, beverages, foods or feeds that are effective in preventing/treating the metabolic syndrome caused by an accumulation of visceral fat—products that can be taken daily and over a long period of time without presenting safety risks—are being desired.

As for the application of lactic bacteria as effective ingredients that act upon human health, Patent Literature 1 reports that lactic bacteria belonging to the *Lactobacillus acidophilus* complex, which are classified as *Lactobacillus acidophilus, Lactobacillus crispatus, Lactobacillus amylovorus, Lactobacillus gasseri, Lactobacillus gallinarum* or *Lactobacillus johnsonii* and has affinity with asialo GM1, as well as extracts of these lactic bacteria, are effective in preventing the infection of pathogens having affinity with asialo GM1.

Also, Patent Literature 2 reports that fungus bodies of *Lactobacillus gasseri* or fermentation products thereof are effective ingredients of preventive/treatment drugs for inflammatory bowel diseases as well as for the irritable bowel syndrome. Furthermore, Patent Literature 3 describes a drug to prevent/improve/treat diabetic complications whose effective ingredient includes lactic bacteria belonging to the *Lactobacillus gasseri* group and cultures thereof, as well as lactic bacteria belonging to the *Bifidobacterium longum* group and cultures thereof.

Among drugs whose effective ingredients are fungus bodies and cultures obtained by culturing lactic bacteria belonging to the *Lactobacillus gasseri* group, a drug to suppress rise in serum cholesterol level is described in Patent Literature 4, in addition to the above. Also, Patent Literature 5 describes an osteoclastic inhibitor, where its effective ingredient includes fungus bodies and cultures thereof obtained by culturing lactic bacteria belonging to the same *Lactobacillus gasseri* group, along with a beverage, food or feed having a bone absorption suppression action. Patent Literature 6 describes an immunologic enhancement agent and an immunologic enhancement beverage or food, each of which does not contain lactic bacteria belonging to the *Lactobacillus gasseri* group alone, but instead blends lactic bacteria belonging to the *Lactobacillus gasseri* group with grains of oat and other members of the Gramineae family as well as processed products made from these grains, where the aforementioned document shows that blending these ingredients activates macrophages more and increases the cytokine production in a synergistic manner to increase the immunologic enhancement effect. However, it is not known that cultures of *Lactobacillus gasseri*, or fungus bodies themselves, have a visceral fat reducing action.

On the other hand, *Lactobacillus helveticus*, which is a lactic bacterium in the *Lactobacillus* sp. and has been used as a representative lactic bacteria starter for dairy products for many years, has strong protein decomposition activity and in particular, the extracellular proteinase of *Lactobacillus helveticus* which exhibits especially high activity has an important action on the fermentation property of milk. To be specific, this extracellular proteinase decomposes lactoprotein and produces various types of peptide fragments. The produced peptides then receive actions of a group of peptitases and further change themselves into peptides of lower molecular weights. It is known that some of the peptides produced in the culture medium due to the actions of a group of proteolytic enzymes are taken into the fungus bodies of lactic bacteria and utilized as a source of nitrogen.

On the other hand, it is reported in Non-patent Literature 1 that some of the peptides produced in the culture medium have an activity to inhibit the angiotensin converting enzyme (hereinafter referred to as "ACE") which is a substance that causes rise in blood pressure. As for peptides intended to inhibit the enzymatic activity of ACE and thereby suppress rise in blood pressure, many effective peptides have already been reported that are produced from lactoprotein, soybean protein or fish/meat protein decomposition products, etc. Among others, the peptides with ACE inhibition activity contained in fermented milk made with *Lactobacillus helveticus* have been revealed as Val-Pro-Pro and Ile-Pro-Pro, and these lactotripeptides have been shown to present a strong hypotensive action in an experiment using rats with naturally induced hypertension (SHR), according to Non-patent Literature 2. As just described, functional foods containing acid milk that has been fermented by Lactobacillus helveticus are also shown to have not only a hypotensive activity, but also a stress relieving action, in Non-patent Literatures 7 and 8. In addition, lactic bacteria such as *Lactobacillus helveticus, Lactobacillus casei, L. delbrueckii* subsp. *bulgaricus, L. delbrueckii* subsp. *lactis*, etc., are shown to provide an immunostimulation action in Patent Literature 9.

However, it is not known that the fungus bodies of these lactic bacteria themselves, or cultures thereof, have a visceral fat reducing action.

*Lactococcus lactis* or *Lactococcus cremoris* are lactic bacteria which are widely used in the manufacture of milk products. However, not much is known about the physiological functions of these lactic bacteria. Although lactic bacteria belonging to the *Lactococcus* sp. are known to produce γ aminobutyric acid (GABA) and the like through fermentation of milk, soybean milk, pickles, etc., to finally demonstrate a blood pressure adjusting action, etc., it is not known that these lactic bacteria contribute to the reduction of visceral fat.

Patent Literature 1: Japanese Patent Laid-open No. Hei 8-268899
Patent Literature 2: Japanese Patent Laid-open No. 2003-95963
Patent Literature 3: Japanese Patent Laid-open No. 2003-252770
Patent Literature 4: Japanese Patent Laid-open No. 2003-306436
Patent Literature 5: Japanese Patent Laid-open No. 2004-315477
Patent Literature 6: Japanese Patent Laid-open No. 2006-69993
Patent Literature 7: Japanese Patent Laid-open No. Hei 10-45610
Patent Literature 8: Japanese Patent Laid-open No. Hei 11-98978
Patent Literature 9: Japanese Patent Laid-open No. 2006-76961
Non-patent Literature 1: J. Dairy Sci., 78: 777-783 (1995)
Non-patent Literature 2: J. Dairy Sci., 78: 1253-1257 (1995)

SUMMARY OF THE INVENTION

Problems to be Solved by the Invention

The present invention aims to provide a visceral fat reducing agent which can be taken daily and when taken, reduces visceral fat and is therefore effective in preventing/treating the metabolic syndrome, as well as a beverage, food or feed to which the function of the aforementioned agent has been added.

Means for Solving the Problems

The inventors of the present invention had worked earnestly to explore ingredients that would lower visceral fat, which is believed to be a cause of the metabolic syndrome, from among the constituents of milk. As a result, the inventors of the present invention found that lactic bacteria, especially lactic bacteria belonging to the *Lactobacillus* sp. and *Lactococcus* sp., present an extremely high visceral fat reducing action, and subsequently completed the present invention.

The aforementioned lactic bacteria belonging to the *Lactobacillus* sp. and *Lactococcus* sp. are used in the manufacture of various fermented foods such as fermented milks, cheeses, pickles, etc. These lactic bacteria are isolated from lactic bacteria used in dairying or from intestinal bacteria in human digestive tracts, and are known to have not only a bowel regulating action, but also many physiological functions such as an immunoregulatory activity, serum cholesterol lowering action, infective disease preventing action, and the like. The present invention provides a visceral fat reducing agent whose effective ingredient includes fungus bodies of these lactic bacteria belonging to the *Lactobacillus* sp. and *Lactococcus* sp. and/or cultures thereof, as well as a beverage, food or feed to which the function of the aforementioned agent has been added.

The aforementioned visceral fat reducing agent can be used in a tablet, powder, capsule or other form. The potential applications of this visceral fat reducing agent include fermented milks, health foods, cheeses and other beverages or foods, and feeds.

The present invention basically encompasses the following constitutions:

(1) A visceral fat reducing agent whose effective ingredient includes fungus bodies of lactic bacteria and/or cultures thereof.

(2) A visceral fat reducing agent according to (1) above, characterized in that its effective ingredient includes lactic bacteria belonging to the *Lactobacillus* sp. and/or *Lactococcus* sp. and/or cultures thereof.

(3) A visceral fat reducing agent according to (2) above, characterized in that its effective ingredient consists of fungus bodies of one or more of *Lactobacillus gasseri, Lactobacillus helveticus, Lactococcus lactis* and *Lactococcus cremoris* and/or cultures thereof.

(4) A tablet, powder, capsule, beverage, food or feed with visceral fat reducing effect, characterized in that it is blended with the fungus bodies of lactic bacteria and/or cultures thereof according to any one of (1) to (3) above.

(5) A beverage or food according to (4) above, characterized in that said beverage or food is a fermented milk, health product or cheese, etc.

Effects of the Invention

A visceral fat reducing agent whose effective ingredient includes fungus bodies of lactic bacteria and/or cultures thereof, as well as a beverage, food or feed to which a visceral fat reducing action has been added by said visceral fat reducing agent contained in it, each of which conforming to the present invention, are effective in preventing/treating the metabolic syndrome which is said to be triggered by an accumulation of visceral fat.

In addition, a visceral fat reducing agent as well as a beverage, food or feed to which a visceral fat reducing action has been added, each of which conforming to the present invention, use cultures of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, or their fungus bodies themselves, and therefore can be supplied in large quantities at relatively low costs and are also extremely safe.

BEST MODE FOR CARRYING OUT THE INVENTION

Examples of lactic bacteria used under the present invention include lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*.

Among the lactic bacteria belonging to the *Lactobacillus gasseri* group, the SBT 2055 strain of *Lactobacillus gasseri*, JCM 1131 strain of *Lactobacillus gasseri*, and ATCC 19992 strain of *Lactobacillus gasseri* could be selected.

Additionally, the SBT 2055 strain has been donated, under Donation Receipt No. FERM ABP-10953, to the International Patent Organism Depository (IPOD) of the National Institute of Advanced Industrial Science and Technology (AIST) (6 Chuo, 1-1-1 Higashi, Tsukuba-shi, Ibaragi-ken; received on Feb. 26, 2008). The JCM 1131 strain is a strain available to public from the Institute of Physical and Chemical Research (RIKEN), while the ATCC 19992 strain is a strain available to public from American Type Culture Collection.

Also among the lactic bacteria belonging to the *Lactobacillus helveticus* group, the SBT 2171 strain of *Lactobacillus helveticus*, ATCC 10386 strain of *Lactobacillus helveticus*, and ATCC 10797 strain of *Lactobacillus helveticus* could be selected.

Additionally, the SBT 2171 strain has been donated, under Donation Receipt No. FERM BP-5445, to the International Patent Organism Depository (IPOD) of the National Institute of Advanced Industrial Science and Technology (AIST) (6 Chuo, 1-1-1 Higashi, Tsukuba-shi, Ibaragi-ken; received on Mar. 6, 1996). Also, the ATCC 10386 strain and ATCC 10797 strain are strains available to public from American Type Culture Collection.

In addition, among the lactic bacteria belonging to the *Lactococcus lactis* group, the JCM 1107 strain of *Lactococcus lactis* and JCM 1107 strain of *Lactococcus lactis* could be selected. Additionally, the JCM 1107 strain of *Lactococcus lactis* is a strain available to public from the Institute of Physical and Chemical Research (RIKEN).

Furthermore, among the lactic bacteria belonging to the *Lactococcus cremoris* group, the ATCC 11602 strain of *Lactococcus cremoris*, ATCC 14365 strain of *Lactococcus cremoris* and ATCC 19257 strain of *Lactococcus cremoris* could be selected. Additionally, the ATCC 11602 strain, ATCC 14365 strain and ATCC 19257 strains are strains available to public from American Type Culture Collection.

It should be noted that, in selecting lactic bacteria, those lactic bacteria which are more suitable for the present invention can be selected if the selection is focused on bacteria strains exhibiting high resistance to gastric acid, good growth in a low-pH condition, high stability in human intestinal tracts, affinity to cells in human intestinal tracts, resistance to bile, ability to remain stable in intestinal tracts, high survivability when applied to foods, and excellent flavor and physical properties.

In particular, the SBT 2055 strain of *Lactobacillus gasseri* (FERM ABP-10953) exhibited high affinity to cells in human intestinal tracts, were able to survive and reach the intestinal tracts when administered orally, and could remain in the intestinal tracts for a long period, where the bacteria grew in the intestinal tracts and acted upon the host, thereby exhibiting high activity including a visceral fat reducing effect. It was never known that lactic bacteria belonging to the *Lactobacillus gasseri* group and administered from outside the body would remain stable in the intestines and exhibit the aforementioned physiological effects, and this has been revealed for the first time by the inventors of the present invention.

In addition, the present invention can use not only the aforementioned bacteria strains, but also *Lactobacillus gasseri* isolated from the human body or fermented milk, regardless of whether the fungus bodies are alive or dead, as long as the fungus bodies exhibit the aforementioned actions. The present invention can also use variant strains of *Lactobacillus gasseri* as long as they exhibit the aforementioned actions.

In addition to the aforementioned *Lactobacillus gasseri* type of lactic bacteria, a similar visceral fat reducing effect is demonstrated by, among others, lactic bacteria used to process milk, such as *Lactobacillus crispatus* belonging to the same Lactobacillus acidophilus group that includes *Lactobacillus gasseri*, or *Lactobacillus delbrueckii* subsp. *bulgaricus* which is a high-temperature homo-type bacterium, as well as *Lactobacillus plantarum* and *Lactobacillus casei* which are medium-temperature homo-type lactic bacteria.

The culture medium used to culture *Lactobacillus gasseri*, which is a lactic bacterium used under the present invention, may be a culture medium containing a lactic culture medium or milk constituents, or any one of various semi-synthetic culture media not containing any lactic culture medium or milk constituents. Examples of these culture media include a reduced skim milk culture medium that has been produced by reducing skim milk and then heating and sterilizing the reduced skim milk.

As for the culture method, these lactic bacteria belonging to the *Lactobacillus* sp. and *Lactococcus* sp. are cultured by means of stationary culture, or by neutral culture where the pH level is controlled at a constant level. However, the culture method is not specifically limited as long as the conditions allow bacteria to grow in a favorable manner. As for fungus bodies, lactic bacteria can be cultured according to a normal method used to culture lactic bacteria, where fungus bodies can be isolated from the obtained culture via centrifugal separation or by other means for collecting bacteria and the isolated fungus bodies can be used directly as an effective ingredient conforming to the present invention. Not only pure fungus bodies that have been isolated, but also cultures, suspensions and other substances containing fungus bodies or cytoplasm or cell wall fractions obtained by processing fungus bodies using an enzyme or other physical means can be used, as well. In addition, not only live fungus bodies, but also dead fungus bodies, can be used.

A visceral fat reducing agent conforming to the present invention contains, as its effective ingredient, cultures of lactic bacteria belonging to the *Lactobacillus* sp. and *Lactococcus* sp. and/or their fungus bodies themselves. In addition, this agent can be prepared into pharmaceutical formulations by adding, as deemed appropriate, diluting agents, stabilizers, flavoring agents and other additives permitted for use in pharmaceutical formulations, after which the mixture may be condensed, freeze-dried or heated and dried to kill the fungus bodies. The present invention also encompasses dried forms, concentrates or pastes of mixtures obtained as described above. Also, diluting agents, binders, disintegrants, lubricants, flavoring/aromatic agents, suspension agents, coating agents and other desired chemical agents can be mixed into these pharmaceutical formulations. As for dosage forms, tablet, pill, capsule, granule, powder, dust, syrup, etc., can be considered, and it is desirable that obtained formulations having these dosage forms be administered orally.

The present invention also provides a beverage, food or feed to which a visceral fat reducing function has been added and whose effective ingredient includes cultures of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, or their fungus bodies themselves. A beverage, food or feed to which a visceral fat reducing action has been added, which conforms to the present invention, may be constituted by cultures of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, or their fungus bodies themselves, or such beverage/food may be prepared by blending the aforementioned fungus bodies or cultures directly. Favorable forms of cultures include yogurt, cheese and other fermented products.

Fungus bodies and cultures can be blended into any beverages and foods, or they can be added to materials used in the manufacturing processes of beverages and foods. Examples of applicable beverages and foods include milk drinks, fermented milks, fruit beverages, jellies, candies, milk products, mayonnaises and other processed egg products, butter cakes and other confectionaries and breads, and the like. Other targets of blending include various powder milks and other nutritional compositions intended for infants, small children and infants of low birth weight, etc. If live fungus bodies are used, fungus bodies of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, may be used or fermented milks or cheeses obtained by fermenting the fungus bodies of the aforementioned lactic bacteria may be used as materials to make breads, snacks, cakes, puddings and other products with visceral fat reducing effect. These lactic bacteria and products can be taken daily and demonstrate a visceral fat reducing action, and therefore they are effective in preventing/treating the metabolic syndrome.

In addition, the present invention provides a feed to which a visceral fat reducing action has been added, where its effective ingredient includes cultures of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, or their fungus bodies themselves. As is the case with beverages and foods mentioned above, these fungus bodies and cultures can also be blended into any feeds for livestock or added to materials used in the manufacturing processes of feeds.

Under the present invention, in order to bring out the visceral fat reducing action, it is sufficient to adjust, among others, the blending quantity of cultures of lactic bacteria belonging to the *Lactobacillus* sp. and lactic bacteria belonging to the *Lactococcus* sp., or especially *Lactobacillus gasseri, Lactobacillus helveticus, Lactococcus lactis* or *Lactococcus cremoris*, or their fungus bodies themselves, so that they can be taken by 10 to 200 g a day in the case of cultures, or by 0.1 to 5,000 mg a day in the case of fungus bodies. The ratio of lactic bacteria content is not specifically limited, and can be adjusted as deemed appropriate according to ease of manufacturing, desired dosage per day, and the like. If the dosage form is liquid, for example, it is desirable that the concentration of lactic bacteria be adjusted to a range of $1 \times 10^5$ cells/ml to $1 \times 10^{10}$ cells/ml. If the dosage form is solid, on the other hand, a desired concentration of lactic bacteria is in a range of $1 \times 10^5$ cells/g to $1 \times 10^{10}$ cells/g. If live bacteria are administered, the intended effect of the present invention can be embodied by administrating $10^8$ to $10^{12}$ cfu per day per adult. When lactic bacteria are taken this way, they will remain stable in the intestinal tracts and demonstrate the desired effects.

The applicants for the present application for patent had earlier filed an application for patent involving a visceral fat accumulation suppressing agent whose effective ingredient includes fungus bodies of lactic bacteria belonging to the *Lactobacillus* sp. and cultures thereof, as well as a beverage or food to which a visceral fat accumulation suppressing action has been added (Toku-Gan 2006-239290). However, the earlier application for patent was intended to suppress accumulation of visceral fat itself and it did not discover any action to reduce accumulated metabolic, which is what the present invention reveals. Also, the present invention is characterized in that it not only improves the individual diseases and conditions associated with the metabolic syndrome more quickly and effectively, but it also finds its effective ingredient in fungus bodies of lactic bacteria belonging to the *Lactococcus* sp. as well as cultures thereof.

A visceral fat reducing agent or beverage, food or feed with visceral fat reducing effect conforming to the present invention has the effect of reducing visceral fat and therefore may prove very effective in preventing, treating and improving the various diseases and conditions triggered by an accumulation of visceral fat as mentioned earlier.

Fungus bodies of lactic bacteria used in the present invention have been utilized since ancient times in the manufacture of fermented milks and cheeses, and therefore any visceral fat reducing agent or beverage, food or feed with visceral fat reducing effect conforming to the present invention is characterized in that it does not present safety problems.

Examples and test examples are presented below to explain the present invention in greater details. However, it should be noted that these examples are given only for illustrative purposes and the present invention is not at all limited to these examples.

EXAMPLE 1

(Preparation of *Lactobacillus gasseri* Culture Powder 1)

A reduced skim milk culture medium (containing skim milk by 13 percent by weight and yeast extract by 0.5 percent by weight) was sterilized for 30 minutes at 95° C., after which the SBT 2055 strain of *Lactobacillus gasseri* (FERM ABP-10953) was inoculated and cultured for 16 hours at 37° C., and then the obtained culture was freeze-dried to obtain a culture powder of the SBT 2055 strain of *Lactobacillus gasseri* (FERM ABP-10953). This powder can be used directly as a visceral fat reducing agent conforming to the present invention.

EXAMPLE 2

(Preparation of *Lactobacillus gasseri* Culture Powder 2)

A reduced skim milk culture medium (containing skim milk by 13 percent by weight and yeast extract by 0.5 percent by weight) was sterilized for 30 minutes at 95° C., after which the JCM 1131 strain of *Lactobacillus gasseri* was inoculated and cultured for 16 hours at 37° C., and then the obtained culture was freeze-dried to obtain a culture powder of the JCM 1131 strain of Lactobacillus gasseri. This powder can be used directly as a visceral fat reducing agent conforming to the present invention.

EXAMPLE 3

(Manufacture of Tablets)

A liquid culture of the SBT 2055 strain of *Lactobacillus gasseri* (FERM ABP-10953) was centrifugally separated for 15 minutes at a speed of 7,000 rpm at 4° C., after which a process of washing the culture with sterilized water and then separating it centrifugally was repeated three times to obtain washed fungus bodies. These fungus bodies were then freeze-dried to obtain a fungus body powder. Next, one part of this fungus body powder was mixed with four parts of skim milk and the obtained powder mixture was compressed and stamped by 1 g at a time using a tablet machine according to a normal method to prepare tablets, each containing 200 mg of fungus bodies of the SBT 2055 strain of *Lactobacillus gasseri* (FERM ABP-10953) conforming to the present invention.

EXAMPLE 4

(Manufacture of Fermented Milk)

The SBT 2055 strain of *Lactobacillus gasseri* (FERM ABP-10953) was cultured in a MRS liquid culture medium (product name: *Lactobacilli* MRS Broth, manufactured by Difco). One percent by weight of each culture liquid in the logarithmic growth period was inoculated to 10 percent by weight of a reduced skim milk (115° C., sterilized for 20 minutes) to which 0.3 percent by weight of a yeast extract has been added, to prepare a mother culture. The mother culture was then mixed with 10 percent by weight of the reduced skim milk, after which 2.5 percent by weight of the resulting mixture was added to a yogurt mix that had been heated for 10 minutes at 100° C. The final mixture was fermented at 37° C. and when the lactic acidity reached 0.85, the mixture was cooled to end the fermentation, to obtain a fermented milk with visceral fat reducing effect conforming to the present invention.

EXAMPLE 5

(Manufacture of Powder)

The SBT 2055 strain of *Lactobacillus gasseri* (FERM ABP-10953) was inoculated to 5 L of a MRS liquid culture medium (product name *Lactobacilli* MRS Broth, manufactured by Difco), after which the culture medium was kept stationary for 18 hours at 37° C. to culture the bacteria. At the end of culture, the culture medium was centrifugally separated for 15 minutes at a speed of 7,000 rpm to obtain a fungus body concentrate of one-fiftieth the volume of the culture medium. Next, this fungus body concentrate was mixed with the same amount of a dispersion medium containing 10 percent by weight of skim milk and 1 percent by weight of monosodium glutamate to adjust the pH level to 7, and then the pH-adjusted concentrate was freeze-dried. The obtained freeze-dried substance was put through a 60-mesh sieve to grade the grains to produce freeze-dried powder. In accordance with the specifications provided under "Powders" in the 13th Revision of the Japanese Pharmacopeia Manual: General Rules on Pharmaceutical Formulations, 1 g of this freeze-dried fungus powder was mixed with 400 g of lactose (Japanese Pharmacopeia) and 600 g of potato starch (Japanese Pharmacopeia), and the ingredients were mixed uniformly to obtain a powder with visceral fat reducing effect conforming to the present invention.

EXAMPLE 6

(Manufacture of Stick-type Health Food)

The culture powder of the SBT 2055 strain of *Lactobacillus gasseri* (FERM ABP-10953) was taken by 30 g and mixed with 40 g of a mixture containing equal amounts of vitamin C and citric acid, 100 g of granulated sugar, and 60 g of a mixture containing equal amounts of corn starch and milk sugar, and the ingredients were mixed. The obtained mixture was put in stick-shaped sachets to produce a stick-type health food with visceral fat reducing effect conforming to the present invention.

EXAMPLE 7

(Manufacture of Natural Cheese)

A material milk whose fat ratio had been adjusted was heated and sterilized for 15 seconds at 75° C. using plates, after which the material milk was cooled to 30° C. and then mixed with 0.01 percent by weight of calcium chloride. Next, the material milk was mixed with 0.7 percent by weight of a commercial lactic bacteria starter (manufactured by Christian Hansen) and 1 percent by weight of the SBT 2055 strain of *Lactobacillus gasseri* (FERM ABP-10953), after which 0.003 percent by weight of rennet was added to solidify the milk and then the solidified mixture was cut and agitated until the pH level fell in a range of 6.2 to 6.1, upon which whey was removed to obtain curd grains. These curd grains were put in a mold and compacted, after which salt was added to produce a natural cheese with visceral fat reducing effect conforming to the present invention.

EXAMPLE 8

(Manufacture of Capsules)

The material was mixed based on the blend of ingredients shown in Table 1 and crushed into pellets, after which the pellets were filled in capsules to produce capsules with visceral fat reducing effect conforming to the present invention.

TABLE 1

| SBT2055 (FERM ABP-10953) | |
| --- | --- |
| Culture powder (Example 1) | 20.0 (in percent by weight) |
| Lactose | 24.5 |
| Soluble starch | 55.0 |
| Magnesium stearate | 0.5 |

EXAMPLE 9

(Manufacture of Beverage)

The material was mixed based on the blend of ingredients shown in Table 2 and filled into containers, after which the contents were heated and sterilized to produce a beverage with visceral fat reducing effect conforming to the present invention.

TABLE 2

| SBT2055 (FERM ABP-10953) | | |
| --- | --- | --- |
| Culture powder (Example 2) | 2.5 | (in percent by weight) |
| Sugar | 7.5 | |
| Citric acid | 0.6 | |
| Apple juice | 10.0 | |
| Water | 79.4 | |

EXAMPLE 10

(Manufacture of Low-fat, Hard Natural Cheese)

Several types of low-fat, hard natural cheeses were manufactured using a material milk whose fat ratio in cheese had been adjusted to a range of 12 to 30 percent by weight. To be specific, a material milk whose fat ratio had been adjusted was heated and sterilized for 15 seconds at 75° C. using plates, after which the material milk was cooled to 30° C. and then mixed with 0.01 percent by weight of calcium chloride. Next, the material milk was mixed with 0.7 percent by weight of a commercial lactic bacteria starter (manufactured by Christian Hansen) and 1 percent by weight of the SBT 2171 strain of *Lactobacillus helveticus* (FERM BP-5445), after which 0.003 percent by weight of rennet was added to solidify the milk and then the solidified mixture was cut and agitated until the pH level fell in a range of 6.2 to 6.1, upon which whey was removed to obtain curd grains. These curd grains were put in a mold and compacted, after which salt was added to produce a gouda cheese type, low-fat, hard natural cheese with visceral fat reducing effect conforming to the present invention.

EXAMPLE 11

(Manufacture of Fermented Milk)

A fermented milk was manufactured using the SBT 2171 strain of *Lactobacillus helveticus* (FERM BP-5445). To be specific, the SBT 2171 strain of *Lactobacillus helveticus* (FERM BP-5445) was cultured for 12 hours at 37° C. using 100 g of skim milk, and the obtained culture was inoculated to 3 kg of an identical but freshly prepared culture medium and cultured for 12 hours at 37° C. At the end of culture, the entire amount of milk was used as a starter to ferment 100 kg of skim milk for 20 hours at 32° C. to obtain a fermented milk with visceral fat reducing effect conforming to the present invention. The viable cell count in this fermented milk produced from the SBT 2171 strain of *Lactobacillus helveticus* (FERM BP-5445) was $8.2 \times 10^8$ cells/g.

EXAMPLE 12

(Manufacture of Yogurt Drink)

The fermented milk obtained in Example 11 was taken by 43 kg and mixed with 4 kg of granulated sugar, 3 kg of water and 0.15 kg of pectin, after which the ingredients were homogenized to obtain 50 kg of a yogurt drink. This yogurt drink had a mild flavorsome taste and pH of 3.6, and the viable cell count in the yogurt drink produced from the SBT 2171 strain of *Lactobacillus helveticus* (FERM BP-5445) was $4.6 \times 10^8$ cells/g.

EXAMPLE 13

A fermented product obtained in the same manner as described in Example 11 was taken by 5 kg and mixed with an equal amount of water, after which the mixture was centrifugally separated on a continuous centrifuge for 20 minutes at a speed of 3,500×G to separate and collect only fungus bodies. To remove the non-fungus-body components from the sediment, 1 kg of water was added and then the mixture was centrifugally separated again and this process was repeated three times. Finally, 20 g of fungus bodies of the SBT 2171 strain of *Lactobacillus helveticus* (FERM BP-5445) was collected.

EXAMPLE 14

A material was mixed based on the blend of ingredients shown in Table 3 to produce a feed with visceral fat reducing effect conforming to the present invention.

TABLE 3

| SBT 2171 (FERM BP-5445) fungus bodies | 2.5 (in percent by weight) |
| --- | --- |
| Skim milk | 13.5 |
| Soybean sludge | 12.0 |
| Soybean oil | 4.0 |
| Corn oil | 2.0 |
| Palm oil | 27.0 |
| Corn starch | 14.0 |
| Flour | 9.0 |
| Bran | 2.0 |
| Vitamin mixture | 9.0 |
| Mineral mixture | 2.0 |
| Cellulose | 3.0 |

TEST EXAMPLE 1

(Confirmation of Visceral Fat Reducing Action)

Various lactic bacteria were used to confirm the visceral fat recuing action.

The 3T3-L1 strain of mouse fat cells was cultured until confluence in an eagle culture medium containing 10% bovine fetus serum conforming to the modified Dulbecco method, after which the culture was processed with trypsin to separate cells from the plastic walls and the separated cells were collected into a centrifuge pipe. The cells were collected via centrifugal separation (1,000×G for 10 minutes), after which the collected cells were dispersed, to a concentration of 2×10⁷ cells/ml, in a phosphoric acid buffer solution (PBS, pH 7.2) containing 0.9 percent by weight of salt. The separated 3T3-L1 cells were transplanted by 1×10⁷ cells (0.5 ml) at a time into mesentery fat tissues of 56 Balb/c nude mice of 3 weeks of age. The mice were fed with a general standard feed CE2 for four weeks and the amount of visceral fat was measured every week using a micro CT apparatus for test animals to confirm an accumulation of sufficient visceral fat. The mice were then fed for four weeks with CE2 feeds containing 0.1 percent of various lactic bacteria and then dissected to measure the amount of visceral fat for evaluation. In this animal test, one group consisted of four mice.

The results are shown in Table 4. It is clear that the amounts of visceral fat in mice that had taken feeds blended with *Lactobacillus lactic* bacteria and *Lactococcus lactic* bacteria are significantly lower than the amounts of visceral fat in mice that had not taken any lactic bacteria or mice that had taken *Streptococcus thermophilis* bacteria.

TABLE 4

|  | Amount of visceral fat (g) |
|---|---|
| *Lactobacillus gasseri* | |
| SBT 2055 strain (FERM ABP-10953) | 1.05 ± 0.67 |
| JCM 1131 strain | 1.12 ± 0.49 |
| ATCC 19992 strain | 1.58 ± 0.62 |
| *Lactobacillus helveticus* | |
| SBT 2171 strain (FERM BP-5445) | 1.22 ± 0.55 |
| ATCC 10386 strain | 1.41 ± 0.39 |
| ATCC 10797 strain | 1.32 ± 0.42 |
| *Lactococcus lactis* | |
| JCM 1107 strain | 1.31 ± 0.31 |
| *Lactococcus cremoris* | |
| ATCC 11602 strain | 1.58 ± 0.56 |
| ATCC 14365 strain | 1.38 ± 0.21 |
| ATCC 19257 strain | 1.44 ± 0.44 |

TABLE 4-continued

|  | Amount of visceral fat (g) |
|---|---|
| *Streptococcus thermophilus* | |
| *Streptococcus thermophilus* ATCC 14485 strain Control group | 2.55 ± 0.33 |
| Not given any lactic bacteria | 2.64 ± 0.62 |

Average ± Standard deviation (n = 4)

What is claimed is:

1. A method of reducing visceral fat of a subject, comprising:
    orally administrating to the subject a composition comprising bacterial cells of lactic acid bacteria belonging to the *Lactobacillus* sp. and/or *Lactococcus* sp. and/or cultures thereof in an amount effective to reduce visceral fat of the subject,
    wherein the lactic acid bacteria are one or more selected from the group consisting of *Lactobacillus gasseri, Lactobacillus helveticus, Lactococcus lactis*, and *Lactococcus cremoris*.

2. The method according to claim 1, wherein the composition is administrated in an amount of $10^8$ to $10^{12}$ cfu per day of the bacterial cells and/or cultures thereof.

3. The method according to claim 1, wherein the administration of the composition is continued until the ingested bacteria remain stable in the intestinal tracts.

4. The method according to claim 1, wherein the subject shows a metabolic syndrome prior to the administration of the composition.

5. The method according to claim 1, wherein the subject is in need of reducing visceral fat.

6. The method according to claim 5, wherein the composition comprises the bacterial cells of lactic acid bacteria and/or cultures thereof as a main active ingredient.

7. The method according to claim 1, wherein the lactic acid bacteria are *Lactobacillus gasseri*.

\* \* \* \* \*

UNITED STATES PATENT AND TRADEMARK OFFICE
CERTIFICATE OF CORRECTION

PATENT NO. : 8,440,179 B2
APPLICATION NO. : 12/525172
DATED : May 14, 2013
INVENTOR(S) : Kawakami et al.

Page 1 of 1

It is certified that error appears in the above-identified patent and that said Letters Patent is hereby corrected as shown below:

On the Title Page

In column 2 (page 1 item 56) at line 9, Under Other Publications, change "article" to --articles--.

In the Specification

In column 1 at line 8, change "English" to --English.--.

In the Claims

In column 14 at line 16, In Claim 1, after "to" delete "the".

In column 14 at line 34, In Claim 6, change "5 ," to --5,--.

Signed and Sealed this
Tenth Day of December, 2013

Margaret A. Focarino
*Commissioner for Patents of the United States Patent and Trademark Office*